United States Patent
Miyoshi

[11] Patent Number: 6,138,522
[45] Date of Patent: Oct. 31, 2000

[54] SAMPLE COLLECTING APPARATUS OF SPACE MACHINE

[75] Inventor: Hiroaki Miyoshi, Tokyo, Japan

[73] Assignee: NEC Corporation, Tokyo, Japan

[21] Appl. No.: 08/827,496

[22] Filed: Mar. 28, 1997

[30] Foreign Application Priority Data

Mar. 29, 1996 [JP] Japan .................................. 8-077610

[51] Int. Cl.⁷ .................................................. E21B 49/00
[52] U.S. Cl. ................................... 73/864.43; 73/863.45; 73/863.56; 73/864.32
[58] Field of Search .......................... 73/864.32, 864.43, 73/864.44, 864.45, 863.41, 863.45, 863.56, 863.71, 863.82, 863.85

[56] References Cited

U.S. PATENT DOCUMENTS

| | | | |
|---|---|---|---|
| 1,927,871 | 9/1933 | Irwin et al. | 73/864.43 |
| 2,361,067 | 10/1944 | Shaw | 73/864.43 |
| 2,435,608 | 2/1948 | Sanford et al. | 73/864.43 |
| 3,416,374 | 12/1968 | Smith | 73/864.43 |
| 3,447,381 | 6/1969 | Langtry et al. | 73/864.43 |
| 3,492,875 | 2/1970 | Tonjes | 73/864.43 |
| 3,822,600 | 7/1974 | Stonner et al. | 73/864.43 |
| 4,345,484 | 8/1982 | Gould et al. | 73/864.43 |
| 5,413,004 | 5/1995 | Johnson, Jr. et al. | 73/864.43 |
| 5,433,121 | 7/1995 | Torra et al. | 73/864.43 |

FOREIGN PATENT DOCUMENTS

5-180737  7/1993  Japan .

*Primary Examiner*—George Dombroske
*Attorney, Agent, or Firm*—Young & Thompson

[57] ABSTRACT

A sample collecting apparatus of a space craft capable of collecting samples securely by collecting them through a single step by using a small size, light weight and simple structure device. The sample collecting apparatus of the space craft includes a canister having a hollow container installed vertically and movably to the space craft, a drill having a spiral shaped groove on an external circumference thereof which passes vertically through a bottom surface of the canister and is protruded and retracted therethrough, while rotating; and a support member for installing the canister and the drill to the space craft so that they can be vertically moved. Expansion and retraction of the support member and rotation and vertical movement of the drill are conducted by a single driving means.

16 Claims, 8 Drawing Sheets

SAMPLE COLLECTING APPARATUS OF SPACE MACHINE

BACKGROUND OF THE INVENTION

1. Field of the Invention

This invention relates to a sample collecting apparatus of a space craft for collecting geological samples of the moon, planets or the like and more particularly to a sample collecting apparatus of a space craft capable of collecting samples securely with only a small, light weight, and simply constructed apparatus.

2. Description of the Related Art

It is very important in the cosmochemistry field to collect and analyze geological samples from geological layers of the moon, planets or the like and investigate a cause of generation of a planet, biological traces or the like.

As such a collecting means for geological samples of planets, for example, a planet geological survey apparatus disclosed in Japanese Unexamined Patent Publication No. 5-180737 has been known.

Figure 8:
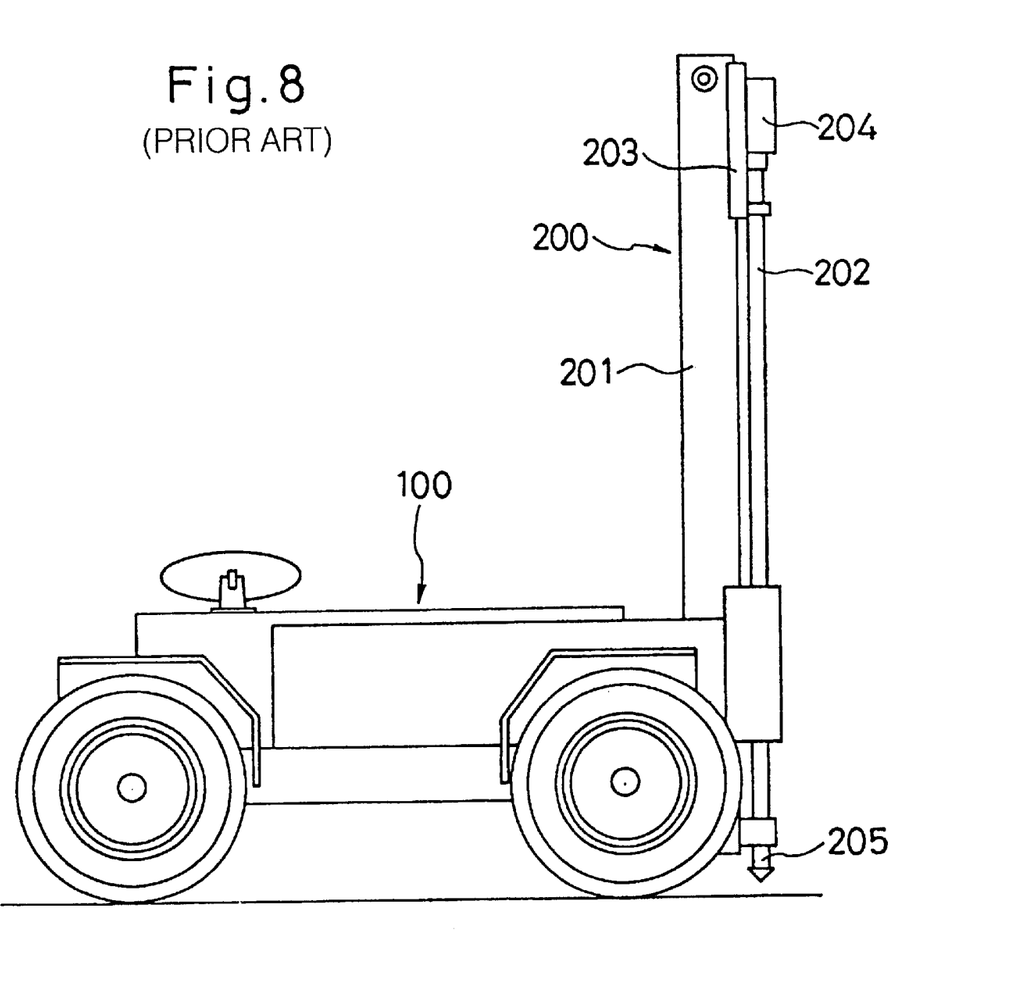
FIG. 8 is an entire side view showing a conventional planet geological survey apparatus.

FIG. 8 is an entire side view showing the planet geological survey apparatus disclosed in Japanese Unexamined Patent Publication No. 5-180737.

As shown in this Figure, this conventional apparatus is so constructed that a sample collecting apparatus 200, a sample transfer apparatus, and a sample analyzing apparatus (not shown) are mounted on a unmanned vehicle 100 which travels by itself on the moon or a planet.

The sample collecting apparatus 200 comprises a guide cell 201 inclinably mounted on the vehicle 100 and a guide pipe 202 mounted to the guide cell 201 so that it is slidably mounted on a progressing unit 203. A rotating shaft (not shown) connected with a rotation driving unit 204 and having spiral blades formed on a circumference thereof is disposed in the guide pipe 202.

A drilling bit 205 having a diameter larger than that of the guide pipe 202 is provided at a front end of this rotating shaft and this drilling bit 205 is protruded from a bottom end of the guide pipe 202.

The sample transfer apparatus (not shown) comprises a conveyor on which a plurality of sample containers are pivotably mounted and wherein each of the sample containers is arranged so as to pass below an opening of a bottom end of the guide pipe in turn, in synchronization with the movement of the conveyor, when the guide cell is inclined, so that the samples which had been picked up from the ground of the planet and kept inside the guide pipe can be distributed into each one of the containers, respectively.

Further, the sample analyzing apparatus (not shown) is provided at an appropriate position in which the sample containers pass.

According to this conventional apparatus, samples are dug by means of the spiral blades provided in the guide pipe 202 and the drilling bit 205 at the front end thereof, and collected in the sample container through a sample conveyor of the sample transfer apparatus. In this manner, geological samples are dug and collected. Further, collected samples are analyzed by the sample analyzing apparatus in the vehicle 100.

As described above, according to the conventional apparatus disclosed in Japanese Unexamined Patent Publication No. 5-180737, geological samples of a planet can be collected, transferred and analyzed by the unmanned space craft.

However, the conventional sample collecting apparatus has the following problems.

A first problem is that the apparatus is of large size and complicated.

That is, in the planet geological survey apparatus disclosed in Japanese Unexamined Patent Publication No. 5-180737, as described above, the sample collecting action is divided into steps of digging, transfer and collection. These actions are conducted by respective independent driving means.

Thus, the conventional apparatus requiring the respective driving means has a problem that the overall size becomes very large and the driving mechanism becomes very complicated, as well.

A second problem is that the reliability in completing sample collection is low.

That is, in a mission carried out outside of a mother spacecraft, sample collecting activity is usually conducted by an unmanned space craft.

Thus, in the space craft having a plurality of independent driving means as in the aforementioned conventional apparatus, the sample collecting activities composed of complicated steps should all be conducted in an unmanned manner. Thus, there is a fear that the reliability of achieving the mission, including the sample collecting activity, may be decreased.

SUMMARY OF THE INVENTION

This invention has been proposed to solve the problems raised in the conventional technology. Accordingly, an object of the present invention is to provide a sample collecting apparatus of a space craft capable of collecting samples securely by collecting the samples through a single step by means of a sample collecting device having a small size, light weight, and a simple construction thereof.

Accordingly, to maintain the above-mentioned object of the present invention, a sample collecting apparatus of the present invention basically has the following technical construction, in that a sample collecting apparatus of space craft comprises a canister comprising a hollow container attached to a part of the space craft and so constructed that a position thereof is changed along a direction from the space craft to the ground surface of a planet; a rotating drill having a spiral groove provided on an external circumference thereof, which is arranged perpendicular to a bottom surface of the canister, and which contacts to the ground surface of the planet and is so constructed to be capable of protruding from the bottom surface of the canister from an interior thereof; and a supporting means for installing the canister and the drill to the space craft so as to be capable of being expanded and retracted.

DETAILED DESCRIPTION OF THE PREFERRED EMBODIMENTS

Hereinafter, an embodiment of a sample collecting apparatus of a space craft according to the present invention will be described in detail with reference to the accompanying drawings.

Figure 1:
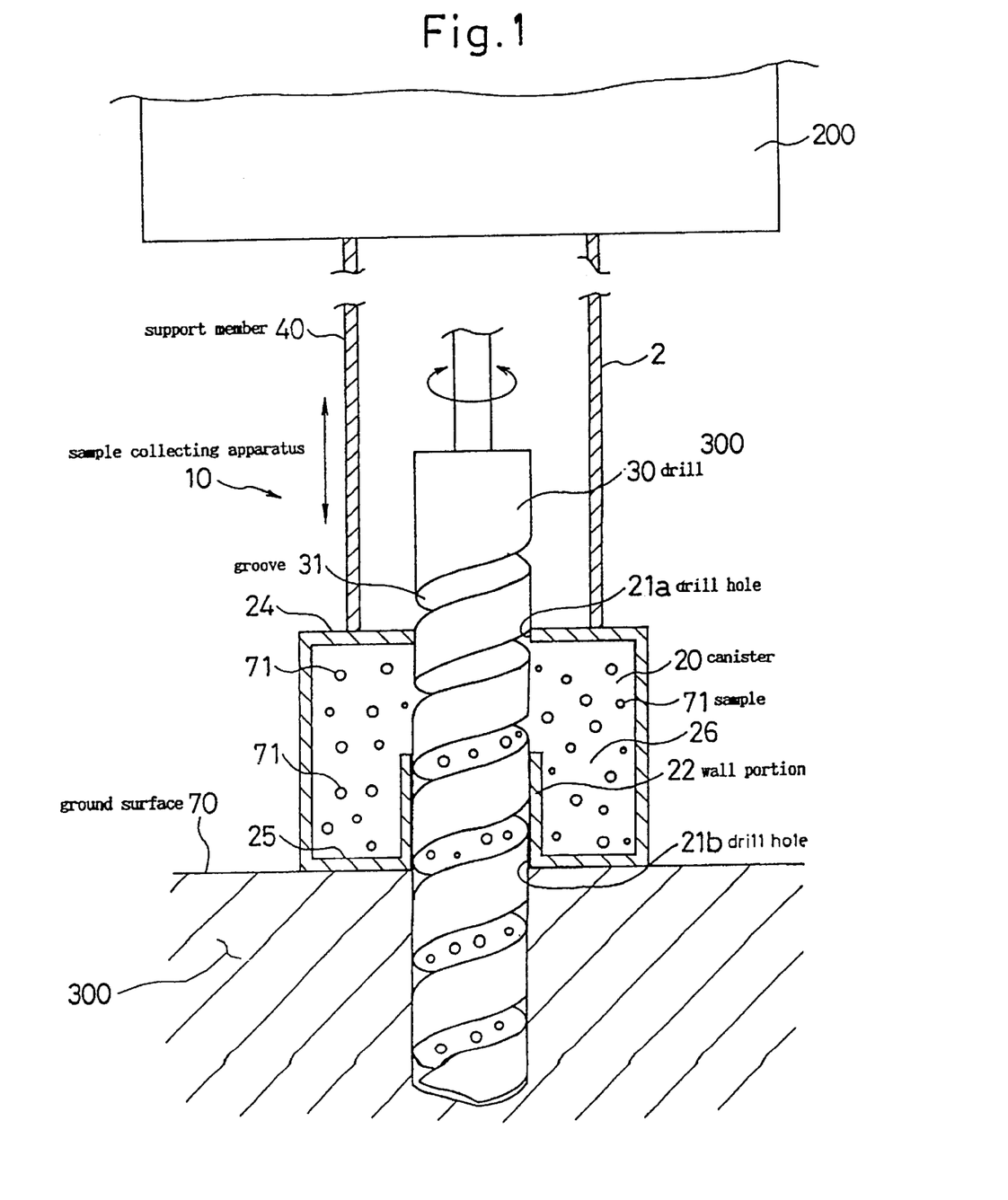
FIG. 1 shows one embodiment of the sample collecting apparatus used in a space craft of the present invention and also shows a partial sectional front view of the apparatus showing it in a step of digging samples.

FIG. 1 shows a construction of one embodiment of a sample collecting apparatus 10 of a space craft 200 according to the present invention.

The sample collecting apparatus 10 of the space craft 200 shown in this Figure comprises a canister 20 which is a hollow container mounted on a part of the space craft 200 and constructed so as to be able to change its position along a direction from the space craft 200 to the ground surface 70 of a planet 300, a rotating drill 30 having a spiral shaped groove 31 formed on an external circumference thereof, which is arranged perpendicular to a bottom surface 25 of the canister 20 contacting the ground surface 60 of the planet 300 and so constructed so as to be able to protrude out of the canister 20 beyond the bottom surface 25 from an internal side 26 thereof, and a supporting member 40 on which the canister 20 and the rotating drill 30 are retractably/expandably mounted relative to the space craft 200.

More concretely speaking, the sample collecting apparatus comprises a canister having a hollow container and movably mounted vertically on the space craft, a drill having a spiral shaped groove which goes through the canister vertically as viewed in FIG. 1 and protrudes/retracts through the bottom surface of the canister while rotating, with the support for mounting the canister and the drill on the space craft being capable of expanding/retracting so that the canister and the drill are vertically movable with respect to the space craft, as shown in FIG. 1.

That is, the space craft 200, including the sample collecting apparatus 10 according to this invention, basically may be any one of a unmanned artificial satellite orbiting in the vicinity of the ground surface of a predetermined planet, a space craft which lands on the ground surface of a predetermined planet and acts as a stationary station, and s space craft which lands on ground surface of a predetermined planet and has a self-traveling function by which it can travel to survey the ground surface of the predetermined planet.

However, it is particularly preferred to be a space craft which rests in space in the vicinity of the ground surface of a predetermined planet and has such a construction for collecting predetermined kinds of information.

In the sample collecting apparatus of the space craft having such a construction according to the present invention, expansion of the support member and rotation of the drill can be effected by mens of a common driving means, and the digging operation for digging on the surface of the planet, the collecting operation for collecting samples, and the storing operation for storing samples can be conducted in a single step.

As a result, the sample collecting apparatus can be constructed having small size, light weight, and using simple structure devices so that samples can be collected and stored securely.

Further, by providing the aforementioned space craft with an attitude control means 60, particularly in stationary type space craft, attitude of the drill and the space craft at the time of digging on a surface of the planet to collect samples can be maintained stably so that collection of samples can be more securely achieved.

Hereinafter, embodiments of the sample collecting apparatus 400 of the space craft 200 according to the present invention will be described in more detail with reference to the accompanying drawings.

FIG. 1 shows one embodiment of the sample collecting apparatus used in a space craft of the present invention and also shows a partial sectional front view of the apparatus indicating when it is in a step of digging samples.

Figure 2:
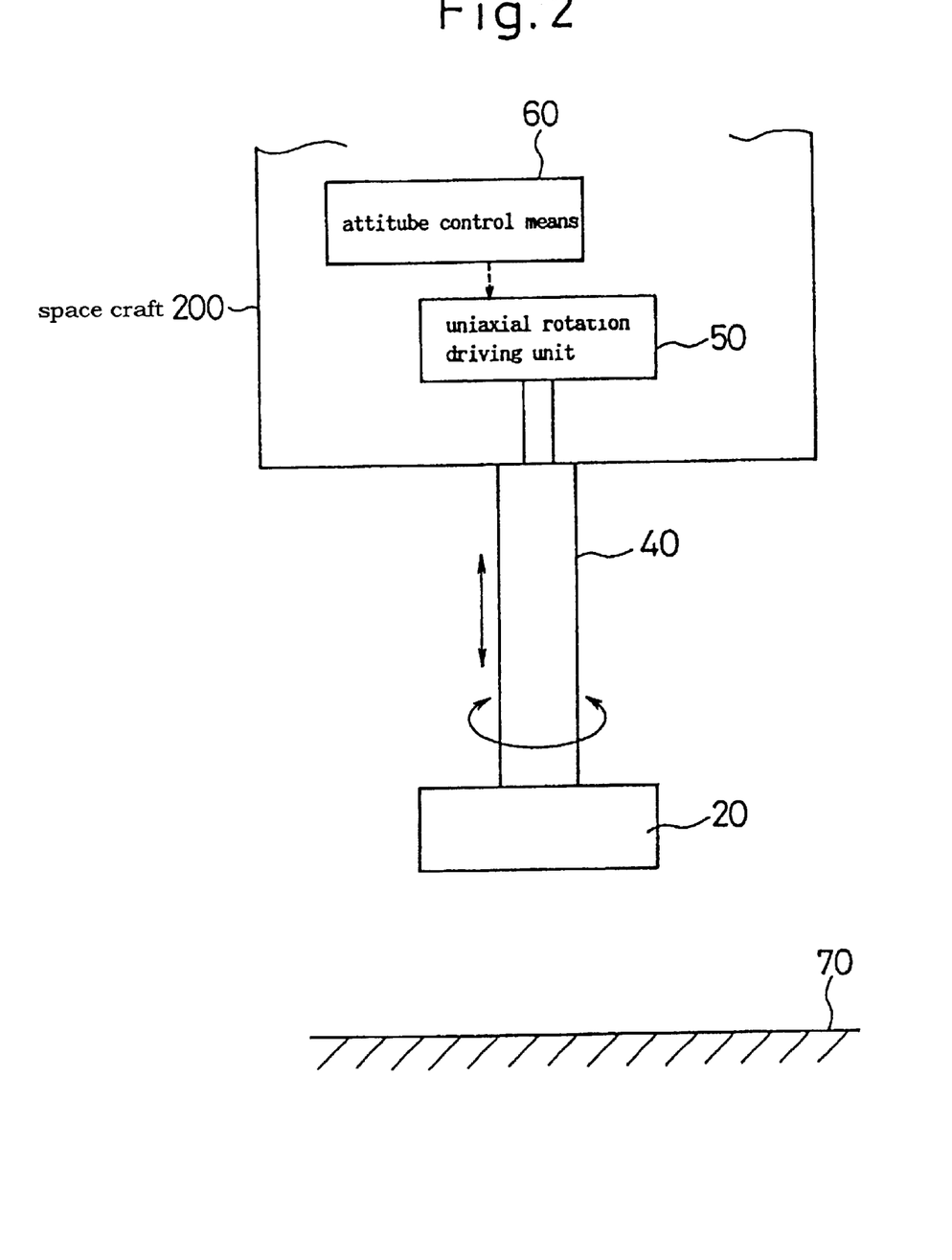
FIG. 2 shows an overall configuration of one embodiment of the sample collecting apparatus used in a space craft of the present invention, and also shows a schematic front view of the apparatus showing it in a step before the digging operation.
Figure 3:
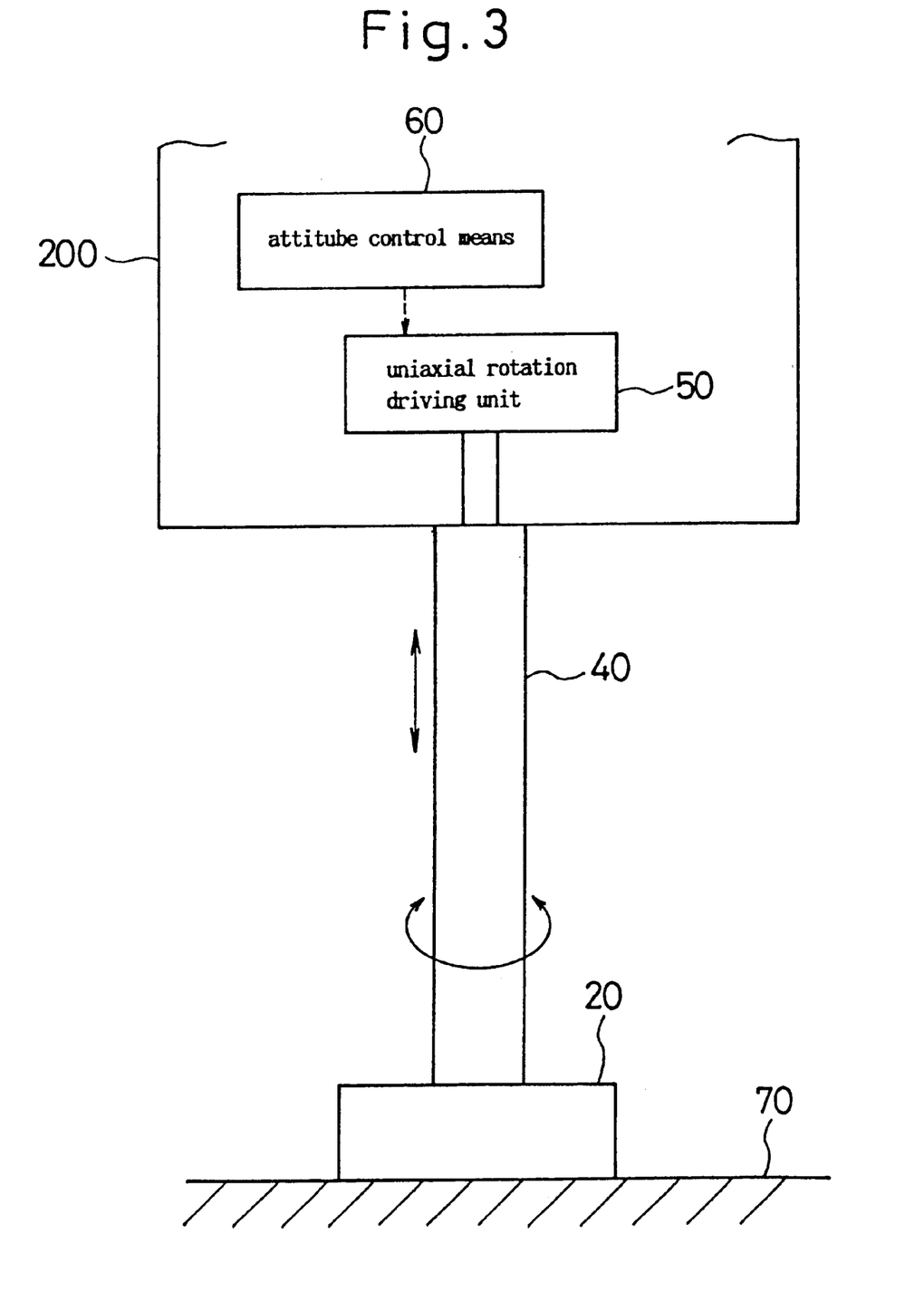
FIG. 3 shows an overall configuration of one embodiment of the sample collecting apparatus used in a space craft of the present invention, and also shows a schematic front view of the apparatus showing it in a step of a digging operation.

And further, FIG. 2 shows an overall configuration of one embodiment of the sample collecting apparatus used in a space craft of the present invention, and also shows a schematic front view of the apparatus indicating when it is in a step before the digging operation, and FIG. 3 shows the same view as shown in FIG. 2, except that the apparatus is in a step of digging a surface of the planet.

Referring to these Figures, reference numeral 10 designates a sample collecting apparatus according to this embodiment.

Generally this sample collecting apparatus 10 is called a "sampler", and mounted on a space craft 200 so that it can ascend or descend freely as viewed in FIG. 1, whereby it can approach or separate from the ground surface 70.

The sample collecting apparatus 10 of one embodiment of the present invention comprises the canister 20 for collecting and storing samples therein, the drill 30 for digging the surface of the planet, and a supporting means 40 for mounting the canister 20 and the drill 30 on the space craft 200, and which is capable of being extended or retracted so as to make them movable along an up/down direction with respect to the space craft, as shown in FIG. 1.

The canister 20 for collecting samples is mounted on a bottom surface of the space craft 200 through the supporting member 40 such that it can be freely moved vertically and is constructed in form of a hollow container as shown in FIG. 1.

In the canister 20, a pair of drill holes 21 (21a, 21b) through which the drill 30 can pass, are formed substantially in the center of a tap face 24 and a bottom surface 25 of the canister 20.

A wall portion 22 is projectingly formed along a peripheral edge of the drill hole 21b provided on the bottom surface 25 of the canister 20 so that it protrudes vertically therefrom and surrounds an external surface of the drill 30 passing through the canister 20.

Consequently, a space 26 separated from the drill hole 21 is formed on a side of the bottom surface 25 of the canister 20. As described later, samples 71 dug by the drill 30 can be stored therein.

The drill 30 for digging samples is so constructed that it passes vertically through the canister 20 and a front end thereof can be projected or retracted through the drill hole 21*b* formed on the bottom surface of the canister 20.

Further, the spiral groove 31 is formed on the external circumference of the drill 30.

As described later, when the drill 30 is rotated to dig the ground surface of a planet, sample 71 thus dug is transferred into the canister 20 along the groove 31.

Further, a root of the drill 30 is coupled with a uniaxial rotary driving unit 50 installed in the space craft 200 and so constructed to be rotated in the center of the support member 40 and slidably moved vertically as viewed in FIG. 1.

The support member 40 is a lifting means which can expand itself to lower the canister 20 from the space craft 200 to the ground surface 70 of a planet to make it approach or detach from a sample object, such as the ground surface of the planet.

As shown in FIG. 1, a front end of the supporting member 40 is attached to a top face 24 of the canister 20, and the root portion thereof is fixedly mounted to the bottom surface of the space craft 200. The drill 30 is disposed in the center thereof.

The drill 30 is coupled with the uniaxial rotation driving unit 50 provided in the space craft 200 so that it can be expanded or retracted along a predetermined direction, for example, in a vertical direction, as shown in FIG. 1, in synchronization with the rotation of this uniaxial rotation driving unit 50.

Thus, the drill 30 may be formed, for example, by a plurality of hollow tube members associated with each other in a telescopic construction.

This uniaxial rotation driving unit 50 is a driving mens for rotational movement and is arranged in the space craft 200 as shown in FIG. 2 and FIG. 3.

As described above, the respective root portions of the drill 30 and the support member 40 are coupled with the uniaxial rotating driving unit 50.

Consequently, the drill 30 and the support member 40 are rotated so as to be expanded or retracted by rotating motion caused by the uniaxial rotation driving unit 50.

The support member 40 is not restricted only to the embodiment as explained above, but it may be of any type of expanding and retracting mechanism, as long as it can move the canister back and force in one direction.

However, according to this embodiment, as described above, the rotating motion of the uniaxial rotation driving unit 50 which rotates the drill 30, causes the support member 50 to expand at the same time.

Thus, a mechanical construction of the support member 40 can be extended and retracted by a rotational motion, for example, a rotary expandable mast or the like can preferably be used.

The rotation type expandable mast mentioned here refers to an expanding means widely used for expanding a solar battery paddle of the space craft.

This kind of expanding means is constructed so that frames thereof can be foldable, and further it can freely expand or fold the frame by utilizing the rotating motion. For example, such a suitable expanding means is disclosed in Japanese Unexamined Patent Publication No. 4-55197, and is called a unit mast.

FIG. 4 to FIG. 7 show an example of the rotation type expandable mast disclosed in Japanese Unexamined Patent Publication No. 4-55197 which is the aforementioned conventional example. This can be used as the support member 40 in this embodiment of the present invention.

As shown in these Figures, in the support member 40 comprising the rotation type expandable mast, according to this embodiment, a driving rod 41 disposed along the center thereof is rotated by the uniaxial rotation driving unit 50, whereby an expanding unit 42 stored in a folded condition is pulled out in its expanding direction (direction indicated by the arrow in FIGS. 4, 5) while rotating so as to form a mast.

Figure 7:
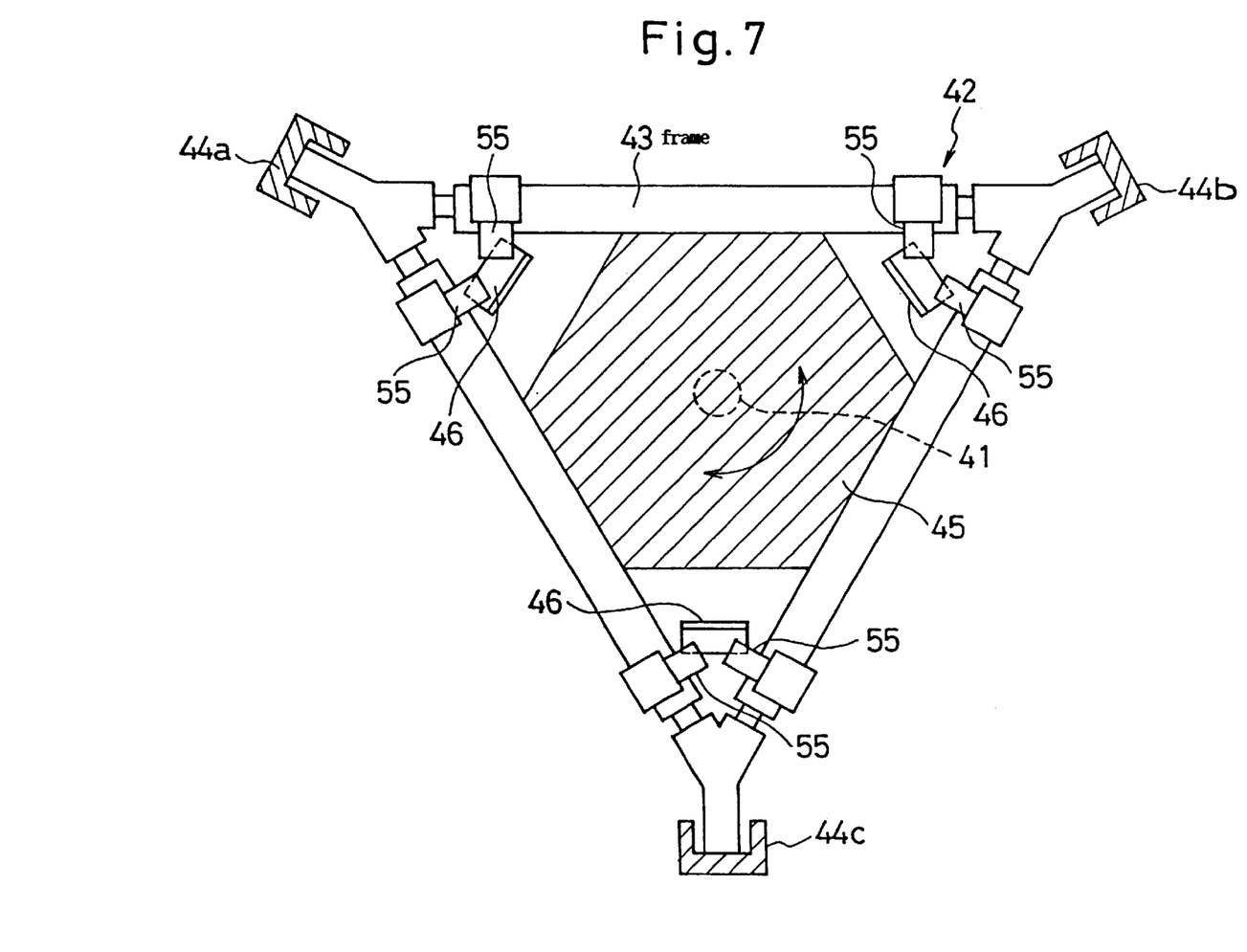
FIG. 7 is a sectional view of a major part of an expanding unit of the support member used in one embodiment of the sample collecting apparatus of the space craft of the present invention.

That is, the expanding unit 42 is so constructed that a plurality of frames 43 each being formed in a configuration of a regular triangle composed of three arms as shown in FIG. 7, are serially interconnected with each other.

Respective vertices of each one of the regular triangles are engaged with the concave guide rails 44 (44*a*, 44*b*, 44*c*).

Figure 5:
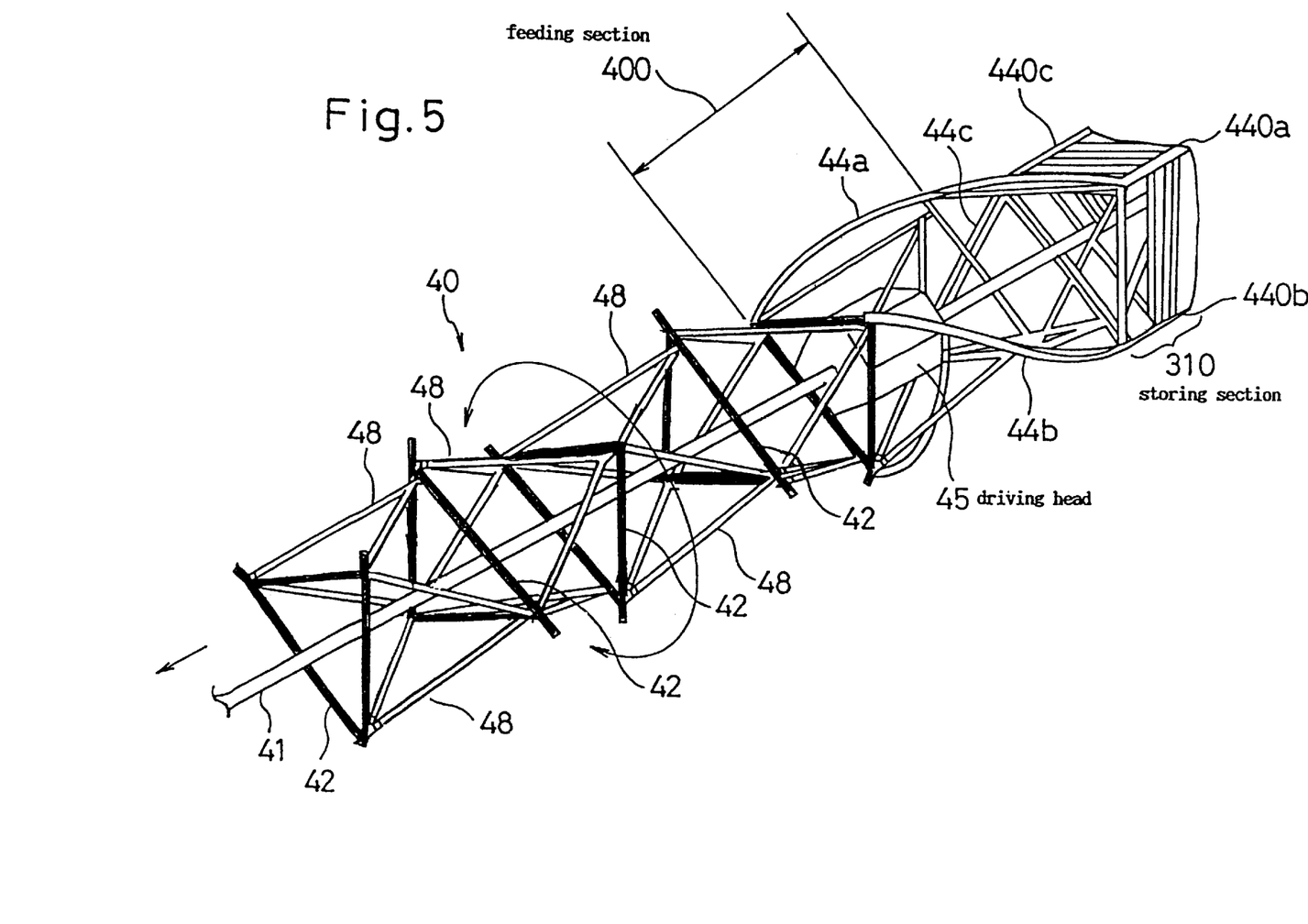
FIG. 5 is a perspective view of a major part of the support member used in one embodiment of the sample collecting apparatus of the space craft of the present invention.
Figure 6:
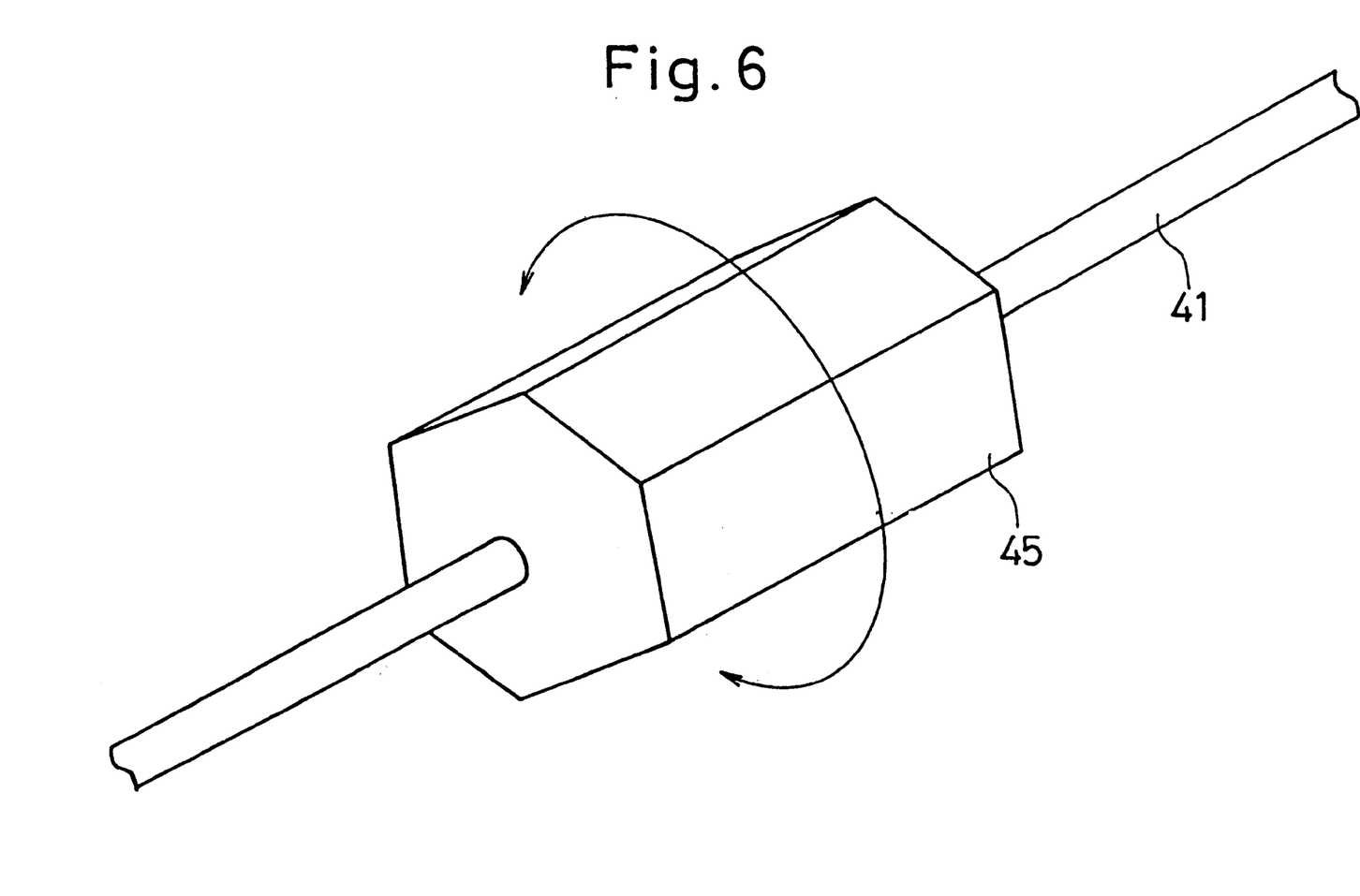
FIG. 6 is a perspective view showing a driving head of the support member according to an embodiment of the sample collecting apparatus of the space craft of the present invention.

Regarding this guide rail 44, one end thereof is fixed to the space craft 200 and the other end thereof is extended by a predetermined length in its expanding direction as shown in FIG. 5, by forming a spiral configuration with an angle of, for example, 60°.

The guide rail 44 guides the respective vertices of the expanding unit 42.

Namely, as shown in FIG. 5, guide rails 440*a*, 440*b*, 440*c* composing a storing section 310 are so arranged to be in parallel to each other. Because the respective vertices of each expanding unit 42 described above are guided in parallel, the expanding units 42 are only moved in parallel translation in a longitudinal direction from the storing section 310.

On the other hand, in a feeding section 400 connected to the storing section 310, the respective guide rails 44*a*, 44*b*, 44*c* are arranged in a spiral shape having an angle of 60° with respect to an axis thereof, and equidistant from each other.

A driving head 45 is disposed along the axis of the feeding section 400, and a first expanding unit 42 is engaged with the driving head 45 as shown in FIG. 7.

Namely, as shown in FIG. 7, the driving head 45 (see FIG. 6) has a hexagonal cross section fixed to the driving rod 41 and is in contact with the internal surfaces of the frames 43 of the expanding unit 42 such that the rotating motion of the driving rod 41 is transmitted thereto.

Consequently, with respect to the support member 40, if the driving rod 41 is rotated by the uniaxial rotation driving unit 50, the driving head 45 mounted in the feeding section 400 is rotated. Then, the driving head 45 and the first expanding unit 42 engaged therewith are rotated, and therefore the first expanding unit 42 is pulled out of the feeding section 400 in a direction indicated by the arrow, while rotating.

Figure 4:
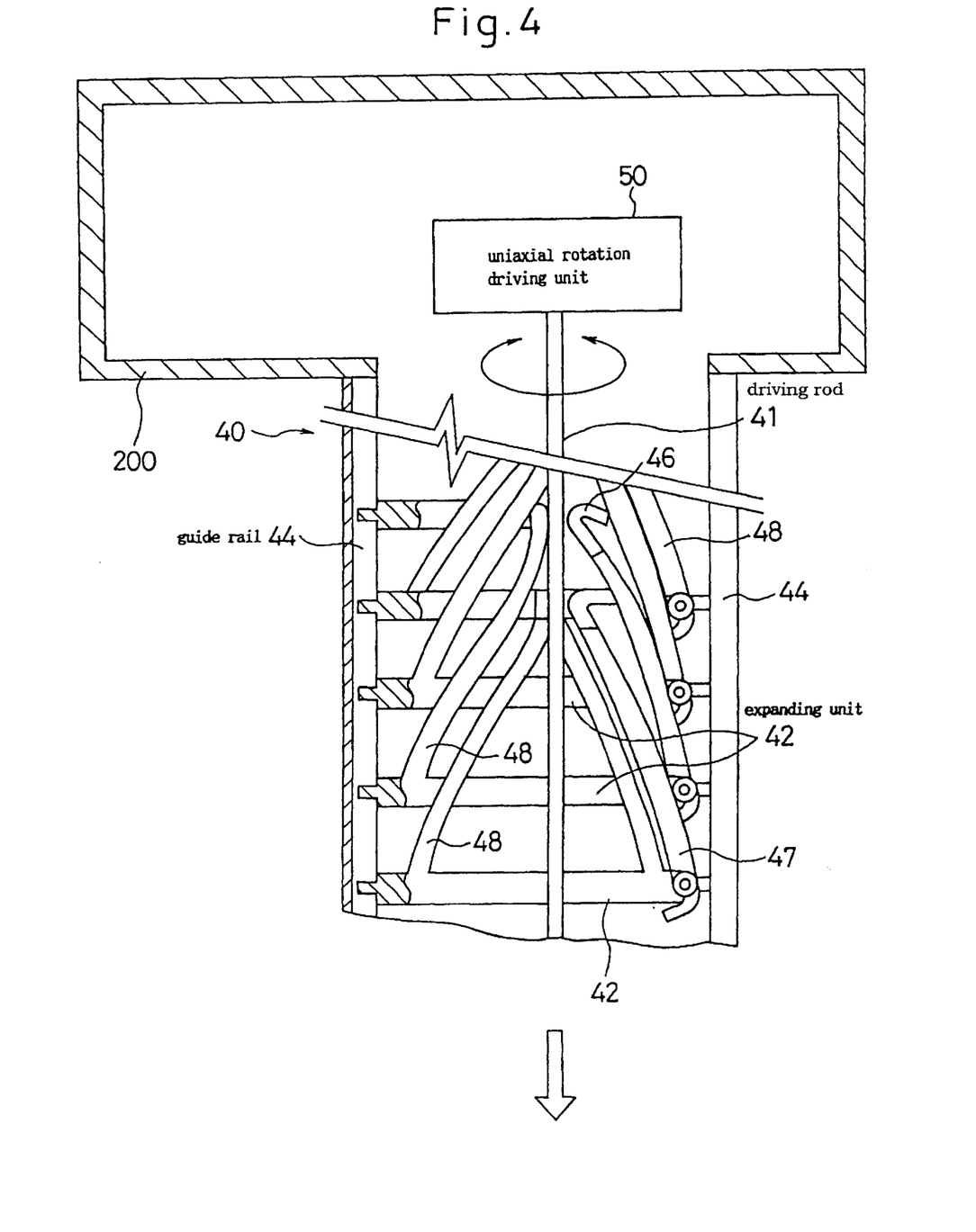
FIG. 4 is a sectional front view of a major part of an expanding structure of a support member used in one embodiment of the sample collecting apparatus of the space craft of the present invention.

At this time, as shown in FIG. 4, the triangle shaped side frames 48 swingably mounted to respective sides of frame 43 of the expanding unit 42 are rotated as well. A hook portion 46 provided at each end of the side frames 48 is engaged with stopper portions 55 provided at each vertex of the triangle of a second expanding unit which is deviated by 120° in phase.

Then, the second expanding unit 42 is pulled out of the storing section 310 and rotated in the feeding section 400.

Thus, with rotation of the driving head 45, a plurality of the expanding units 42 stored in the storing section 310 are successively pulled out due to the engagement of the hooked portion 46 of the side frames 48 with the stopper portions 55.

Consequently, as shown in FIG. 5, the support member 40 forms the expanded condition. Further, the above described activities are conducted in reverse by rotation of the driving head 45 in an opposite direction.

Then, the expanding units 42 are successively stored in the storing section 310 and then the support member 40 is allowed to retract.

Although not shown in this embodiment, the drill 30 is disposed at the front end of the driving rod 41 in this support member 40. As a result, the expanding of the support member 40 and the rotation of the drill 30 can be achieved by the common uniaxial rotation driving unit 50.

Further, as shown in FIGS. 2 and 3, the attitude control means 60 is provided in the space craft 200. This unit is important particularly for the space craft 200 which hovers off the ground surface of a planet while collecting samples therefrom.

This attitude control means 60 maintains an attitude of the space craft 200 in an appropriate condition when the canister 20 and the drill 30 are moved vertically. Generally, spin type or triaxial type attitude control means is used.

That is, this is used as a means for canceling reactions caused by expanding/retracting of the canister 20, the drill 30 and the support member 40 or rotations of the drill 30 as well as for maintaining the resting position of the space craft 200.

Next, operations of the sample collecting apparatus of the space craft according to the present embodiment having such a construction will be described with reference to FIG. 1 and FIG. 3.

First, the space craft 200 approaches an object on a planet which is an object of survey, in so called rendezvous manner.

After the space craft 200 has approached the object, the uniaxial rotation driving unit 50 is driven to expand the support member 40, thereby lowering the canister 20 toward the ground surface 70 as shown in FIG. 2.

At this time, the attitude of the space craft 200 at the time when the support member 40 is expanded is controlled so as to be stabilized by the attitude control means 60.

At this time, the drill 30 is kept stored within the support member 40 and the canister 20.

When the uniaxial rotation driving unit 50 is driven to rotate in a state in which the canister 20 is in contact with the ground surface 70 (state shown in FIG. 3), as shown in FIG. 1, the drill 30 is lowered so as to project from the bottom surface of the canister 20 and be moved into the ground surface 70 to dig the surface of the ground of the planet while the canister 20 is kept in a stationary condition and in contact with the ground surface 70.

Consequently, the ground surface being sampled is crushed into particles, and the samples 71 are carried up through the spiral groove 31 formed on the surface of the drill 30, so that they are removed in a direction opposite to the drilling direction.

After being brought up through the groove 31, the samples 71 enter the canister 20 fixed to a surface of the object and are diffused into the canister 20 at a position at which the wall 22 ends.

At this time, because the drill 30 is rotating at high speeds, the samples 71 are diffused entirely into the canister 20 by means of centrifugal force generated by this rotating motion so that they are collected securely.

Although according to the present embodiment, a single canister is utilized, it is possible to use a plurality of the canisters in such a manner that they are stacked one by one. Consequently, different kinds of samples can be collected.

After sample collection is finished, the uniaxial rotation driving unit 50 is rotated in reverse to retract the support member 40, thereby raising the canister 20. Then, the canister 20 is stored in the space craft 200 and then the samples 71 stored in the canister 20 are sent into the space craft 200.

Further, according to this invention, it is preferable that after the bottom surface of the canister extending from the space craft comes into contact with a predetermined surface of the ground, the drill is protruded out from the bottom surface of the canister.

As described above, in the sample collecting apparatus 10 of the space craft according to the present embodiment, expansion of the support member 40 and rotation of the drill 30 can be conducted by the common uniaxial rotation driving unit 50. Thus, the sample collecting apparatus can be so constructed to have small size, light weight and a simple structure.

Further, in the sample collecting apparatus of the space craft according to the present embodiment, the mechanical driving process of the apparatus is achieved by linear motion imparted by uniaxial rotation, the driving structure is simple and a series of the sample collecting procedure is completed in a single step. Thus, the reliability of achieving the mission of collecting samples by means of the unmanned space craft can be maintained at a very high level.

Still further, in this apparatus, collecting samples into the canister 20 is conducted by only the rotating motion of the drill 30, and all the dug samples are placed into the canister 20. Thus, the samples can be collected securely even in space without gravity and the phenomenon that broken pieces are scattered around so as to damage the space craft or cause contamination or the like will not occur.

As a result, the reliability of achieving the mission by means of the space craft can be raised.

As described above, the sample collecting apparatus of the space craft according to the present invention is capable of collecting the samples securely by collecting them through a single step by means of the small size, light weight and simple structure devices.

What is claimed is:

1. A sample collecting apparatus of a space craft, comprising:
    a canister comprising a hollow container attached to a part of the space craft and so constructed that a position of said canister is capable of being moved in a direction from the space craft to a ground surface of a planet being sampled;
    a rotating drill having a spiral groove on an external surface thereof, said rotating drill being arranged perpendicular to a bottom surface of said canister, said bottom surface for contacting the ground surface of the planet, and said rotating drill being constructed to be capable of protruding from said bottom surface of said canister from an interior of said canister;
    a supporting means for attaching said canister and said rotating drill to the space craft,
    wherein said supporting means, said canister, and said rotating drill are capable of being extended and retracted between a retracted storage position and an extended operating position; and
    a common drive unit imparting uniaxial rotational motion to said supporting means for driving said canister and said rotating drill.

2. A sample collecting apparatus of a space craft according to claim 1, wherein the space craft is one selected from the group consisting of a space craft capable of resting in space off the ground surface of a planet by a predetermined distance, a space craft grounded on the planet and being fixed on the ground surface thereof and a space craft grounded on the planet and being capable of traveling by itself on the ground surface thereof.

3. A sample collecting apparatus of a space craft according to claim 1, wherein an extending and retracting operation of said supporting means and said rotating drill, and a rotating operation of said rotating drill are effected by said common drive unit mounted on the space craft.

4. A sample collecting apparatus of a space craft according to claim 1, wherein said canister further comprises an inside wall portion along a circumference of a hole through said bottom surface of said canister through which said rotating drill passes, and which covers at least a part of said external surface of said rotating drill.

5. A sample collecting apparatus of a space craft according to claim 1, wherein a plurality of said canisters are stacked along an axial direction of said rotating drill.

6. A sample collecting apparatus of a space craft according to claim 1, wherein said space craft is provided with an attitude control means for properly aligning said canister and said rotating drill with the ground surface.

7. A sample collecting apparatus of a space craft according to claim 1, wherein said rotating drill in an operating condition protrudes from said bottom surface of said canister after said bottom surface of said canister comes into contact with the ground surface of a planet.

8. A geological sample collecting apparatus comprising:
a canister comprising a hollow container for collecting geological samples and having a bottom surface for contacting a surface being sampled;
a drill having a spiral groove extending lengthwise along an external surface of said drill,
said drill being arranged perpendicularly to said bottom surface and extending through a hole in said bottom surface when the geological sample collecting apparatus is in an operating condition;
an extensible support mechanism for moving said canister and said drill from a compact stowage position to an extended sampling position located on the surface being sampled and for retractably moving said canister and said drill from the sampling position into the compact stowage position; and
a common drive unit for driving said canister and said drill between the sampling and compact stowage positions and for rotating said drill,
wherein said common drive unit imparts uniaxial rotational motion to said extensible support mechanism.

9. The geological sample collecting apparatus of claim 8, wherein said hollow container comprises a raised flange portion surrounding said hole in said bottom surface and rising above said bottom surface to form a partition within said canister to contain the geological samples collected by the geological sample collecting apparatus.

10. The geological sample collecting apparatus of claim 8, further comprising a support structure for attaching the geological sample collecting apparatus to a moveable vehicle.

11. The geological sample collecting apparatus of claim 10, further comprising an attitude control mean for aligning and stabilizing said moveable vehicle with respect to the surface being sampled.

12. The geological sample collecting apparatus of claim 11, wherein said moveable vehicle is one selected from the group consisting of a self-propelled ground-mobile platform, a hovering spacecraft, and a stationary spacecraft located on a surface of a planet.

13. The geological sample collecting apparatus of claim 8, further comprising a plurality of canisters arranged along an axial direction of said drill for collecting geological samples, wherein said drill passes through a bottom of each of said plurality of canisters and into the surface being sampled.

14. A geological sample collecting apparatus, comprising:
a canister comprising a hollow container for collecting geological samples and having a bottom surface for contacting a surface being sampled;
a drill having a spiral groove extending lengthwise along an external surface of said drill,
said drill being arranged perpendicularly to said bottom surface and extending through a hole in said bottom surface when the geological sample collecting apparatus is in an operating condition; and
an extensible support mechanism for moving said canister and said drill from a compact stowage position to an extended sampling position located on the surface being sampled and for retractable moving said canister and said drill from the sampling position into the compact stowage position,
wherein said extensible support mechanism comprises
a plurality of extending units;
a storage section for storing said plurality of extending units when said canister and said drill are in the compact stowage position, and
a feeding section for receiving said plurality of extending units from the storage section and for extending said plurality of extending units into an extended position in a direction toward and perpendicular to the surface being sampled,
said feeding section having a driving head connected to and driven by a driving rod rotated by said common drive unit for sequentially transmitting a rotary motion to each of said plurality of extending units,
said each of said plurality of extending units being initially extending along a plurality of helical guide rails designed and adapted to transform the rotary motion of each of said plurality of extending units into a linear extension motion in a direction toward the surface being sampled.

15. The geological sample collecting apparatus of claim 14, wherein said driving head has a hexagonal cross-section in a plane orthogonal to a longitudinal direction of said driving rod.

16. The geological sample collecting apparatus of claim 14, wherein each of said plurality of expanding units has a triangular cross-section in a plane orthogonal to a longitudinal direction of said driving rod when the sample collecting apparatus is in an extended position.

* * * * *